United States Patent [19]

Leseur et al.

[11] Patent Number: 4,605,531

[45] Date of Patent: Aug. 12, 1986

[54] PROCESS FOR EXAMINING A FUEL ASSEMBLY OF A NUCLEAR REACTOR AND AN EXAMINING MACHINE FOR PERFORMING THIS PROCESS

[75] Inventors: André Leseur, Bures sur Yvette; Pierre Delaroche, Velizy; Robert Saglio, Antony; Yves Vaubert, Gif sur Yvette, all of France

[73] Assignee: Commissariat a l'Energie Atomique, Paris, France

[21] Appl. No.: 442,645

[22] Filed: Nov. 18, 1982

[30] Foreign Application Priority Data

Nov. 25, 1981 [FR] France .................. 81 22063

[51] Int. Cl.[4] .......................................... G21C 17/00
[52] U.S. Cl. .................................. 376/252; 376/251
[58] Field of Search ............... 376/248, 252, 249, 251; 73/640

[56] References Cited

U.S. PATENT DOCUMENTS

| | | | |
|---|---|---|---|
| 2,594,970 | 4/1952 | Monk | 376/248 |
| 3,107,521 | 10/1963 | McClure | 73/640 |
| 3,114,799 | 12/1963 | Waters et al. | 376/248 |
| 3,229,577 | 1/1966 | Ellinger | 376/248 |
| 4,036,686 | 7/1977 | Weilbacher et al. | 376/251 |
| 4,169,758 | 10/1979 | Blackstone et al. | 376/246 |
| 4,193,843 | 3/1980 | Womack et al. | 376/252 |
| 4,229,069 | 10/1980 | Motin et al. | 376/248 |
| 4,255,762 | 3/1981 | Takeyasu et al. | 376/248 |
| 4,284,473 | 8/1981 | Kasama | 376/248 |
| 4,290,849 | 9/1981 | Vesugi et al. | 376/252 |
| 4,302,286 | 11/1981 | Lefebvre et al. | 376/249 |
| 4,302,772 | 11/1981 | Gillot | 376/248 |
| 4,464,332 | 8/1984 | Boisseuil et al. | 376/248 |

FOREIGN PATENT DOCUMENTS

| | | | |
|---|---|---|---|
| 1140740 | 12/1962 | Fed. Rep. of Germany | 376/248 |
| 3020105 | 5/1980 | Fed. Rep. of Germany | 376/248 |
| 2395571 | 1/1979 | France . | |
| 948003 | 10/1959 | United Kingdom | 376/248 |
| 2014311 | 8/1979 | United Kingdom . | |

OTHER PUBLICATIONS

S 6016 0114 R (9/75) Pulfer.
Post–Irradiation Examination, L. V. Corsetti et al, "The Combustion Engineering Comprehensive Fuel Inspection Stand".

Primary Examiner—Salvatore Cangialosi
Attorney, Agent, or Firm—Oblon, Fisher, Spivak, McClelland & Maier

[57] ABSTRACT

Process and apparatus for examining a fuel assembly of a nuclear reactor. The apparatus includes a support on which is positioned the assembly to be examined, a wave transmitting source directed towards the assembly to be examined, a mechanism for examining the assembly receiving the waves transmitted by the source and which have been reflected by the assembly. The examining mechanism includes a spindle directed towards a mirror, which is inclined in such a way that it reflects the waves reflected by the assembly towards the examining mechanism, and a device for providing protection against radiation emitted by the assembly, the device being positioned between the assembly and the examining mechanism.

16 Claims, 5 Drawing Figures

PROCESS FOR EXAMINING A FUEL ASSEMBLY OF A NUCLEAR REACTOR AND AN EXAMINING MACHINE FOR PERFORMING THIS PROCESS

BACKGROUND OF THE INVENTION

The present invention relates to a process for examining a fuel assembly of a nuclear reactor and to an examining apparatus for performing this process.

It is known that during the operation of a nuclear reactor, particularly a water-cooled reactor, it is necessary to periodically check the fuel assemblies forming the reactor core. This check particularly serves to detect possible deformations of the fuel rods and/or the maintainance structure, the spacing of the rods and any possible risk of cracks. When the reactor is shut down, certain assemblies which have operated under pressure and high temperature are discharged and transferred with the aid of appropriate handling equipment to an examining machine used for checking them.

The prior art describes numerous designs of examining machines for nuclear reactor fuel assemblies.

For example, French Pat. No. 2 298 859, filed on Jan. 22, 1975 and entitled "Apparatus and Installation for Examining the Fuel Rods of a Nuclear Reactor" describes a machine of this type. It comprises examining means making it possible to collect information on the assembly to be examined, means for displacing the examining means with respect to the assembly to be examined and finally means for processing the information collected by the examining means.

The examining means are constituted by a prismatic endoscope, the means for displacing the endoscope being constituted by three moving carriages, the first moving vertically on slides parallel to the fuel rods of the assembly, the second moving horizontally on slides carried by the first carriage and the third moving horizontally perpendicular to the aforementioned carriage. Thus, the endoscope carried by the third carriage can be displaced in three perpendicular directions.

However, a disadvantage of a machine of this type is that the fuel assembly to be examined is held between two ends supports, which rigidly maintain it. These end supports exert stresses on the assembly. However, it is known that the frame of a fuel assembly is of a lightweight construction and easily deforms. Visual observation of the assembly and its metrology are therefore carried out after it has been deformed, so that the measurements are falsified.

According to another design, the measurement and examination of the assembly can be carried out when the latter is suspended by its upper end member. In this case once again the position of the assembly differs from the reference position used in metrology, because it is exposed to tensile stresses. However, the frame formed by the guide tubes is of a lightweight nature and is therefore liable to deform. Thus, the measurements will also be falsified if they are performed when the assembly is extended.

SUMMARY OF THE INVENTION

The present invention relates to a process for examining a fuel assembly of a nuclear reactor, which obviates the aforementioned disadvantage. This process makes it possible to examine the assembly in a position where it rests, without stress, on a reference support block. More specifically, the assembly to be examined is placed vertically on the support block on which it freely rests. It is only exposed to the stresses resulting from its own weight. Thus, it is located in the reference position used for the metrology of the fuel assemblies. Thus, this examination process permits a maximum accuracy of metrology of the fuel assembly.

More specifically, the present invention relates to a process for examining a fuel assembly, wherein the assembly to be checked, suspended on a handling means, is brought to a support, placed vertically on said support, the assembly being in equilibrium on its base, a safety means is introduced which is located at a given level, said safety means not being in contact with the assembly, but retaining it in the case where the assembly moves out of its equilibrium position.

According to a preferred embodiment of the process for examining a nuclear reactor fuel assembly according to the invention the examining means are displaced vertically with respect to the assembly to be examined by moving apart the safety means located at a different level to permit the passage of the examining means, the assembly being safely held during this operation by safety devices at a different level.

The invention also relates to a machine for performing the examining process according to the invention, which comprises a frame on which is arranged a support for receiving the base of the assembly and means for centering said base with respect to said support, wherein such includes at least one pair of safety devices located at a given level, said pair of safety devices being displaceable with respect to the frame, so as to be placed around the assembly and to hold it in the case when it could become unbalanced.

The safety means enclose the assembly without contact during its examination. In order to permit this examination to take place over the entire height of the assembly safety devices are provided at different levels. These safety devices alternately move back to permit the passage of the carriage carrying the examining means over the entire height of the assembly.

Moreover, in order to permit the examination of the entire height of the fuel assembly, including that area level with the lower end part on which it rests, the invention also relates to an examining machine, provided with retractable guidance means. Thus, it is known that a fuel assembly to be examined is centered with respect to its lower support by centering means in the form of a square based frustum. The widened part of the frustum points upwards. The base of the assembly enters it during the presentation of the assembly. The base is automatically centered with respect to centering pins provided on the support block.

It is also known to provide a rotatable support block, so as to successively examine the four lateral faces of the assembly.

According to a feature of the invention, the guidance means are retractable so as to permit the rotation of the support block on which the assembly is located and consequently the lateral faces of its base. Thus, it is possible to examine the entire height of the assembly and take reference measurements on the support block. Preferably the guidance means are in at least two parts, whereby said parts can move away from the base of the assembly so as to permit an examination of the entire height thereof.

Moreover, the fact that the guidance means are retractable, makes it possible to rotate the assembly support and consequently successively examine the four faces of the assembly.

In addition, according to another feature of the invention, protection of observation means against the radiation emitted by the assembly is possible. Thus, it is known that an irradiated fuel assembly emits radiation, which damages the observation or metrology means. For example, a television camera, even such a camera designed to operate under radiation, has a limited life. The protection of the observation means according to the invention significantly increases their life. It is applicable to examination means constituted by a wave source directed towards the assembly and a receiver receiving the waves reflected by the assembly. The processing of the waves received makes it possible to obtain information thereon as a result of subsequent processing.

This protecton device comprises a mirror inclined relative to the face of the assembly to be observed and preferably by 45°. This mirror reflects the waves transmitted by the wave source and greatly reduces the irradiation of the examining means. Preferably, it is transparent to ionizing radiation. The wave receiver is oriented transversely to the emitted radiation and is placed behind a protective plate.

More specifically, the invention relates to a machine for examining a fuel assembly of a nuclear reactor comprising a source for transmitting waves directed towards the assembly to be examined, means for examining the assembly, which receives the waves transmitted by the source and which are reflected by the assembly. The examining machines comprise a spindle, which is directed towards a mirror, which is inclined in such a way that it returns the waves reflected by the assembly to the examining means, a device providing protection against the radiation emitted by the assembly being positioned between the latter and the examining means.

When the examining means are constituted by a television camera, which permits the visual observation or metrology of the assembly, the wave emitting source is a light source by means of which the assembly is illuminated. The light reflected by the assembly is received by the television camera after being reflected by the mirror. In view of the fact that the television camera is located behind a protection device, it is not exposed to the direct radiation emanating from the assembly. Thus, its life is significantly increased.

The examining means may also be constituted by an ultrasonic receiver, in which case the wave transmitting source is an ultrasonic transmitter. The transmitter and receiver can be combined.

Finally, the invention relates to a machine for examining a fuel assembly in which an ultrasonic transmitter-receiver pair is used for collecting information on the assembly to be examined. The ultrasonic transmitter is a focused transmitter. For example, its focal length can be approximately 200 mm, whilst the beam diameter at the focus is approximately 1 mm. This ultrasonic beam is directed perpendicular to the face to be examined. The echo reflected by the different constituent parts of the assembly is received by an ultrasonic receiver. This signal is then recorded, e.g. on a magnetic support. The subsequent processing of these signals, which does not form part of the actual invention, makes it possible to deduce a large number of measurements connected with the characteristics of the assembly. On moving the transmitter-receiver pair perpendicular to one of the faces of the assembly, the processing of the echo received makes it possible to determine the position of the different constituent parts of the assembly, e.g. fuel rods successively encountered along the displacement direction. Moreover, the duration of the outward and return path of the ultrasonic beam makes it possible to determine the position of the different constituent parts of the assembly, as a function of a direction perpendicular to the displacement of the transmitter-receiver pair. It is possible to deduce therefrom the kinking and arching of the assembly.

This examination process for a fuel assembly is advantageous compared with the prior art processes because it makes it possible to accurately measure these dimensions. Moreover, contrary to devices having mechanical sensors, this measurement is carried out without any contact, thereby obviating any risk of starting up defects in part of the assembly. Thus, it can be used for the metrology of an assembly which has to be reloaded. Unlike a television camera, it is not dependent on the illumination or lighting and permits a more accurate measurement. Finally, it operates under water, so that it can be used e.g. in the loading well or pit of flasks for transporting irradiated fuel assemblies. It is merely necessary for the medium in which it is used to be an ultrasonic conductor.

The ultrasonic metrology process according to the invention can obviously be used in the case of a new assembly. It can also be used in combination with the protection device described hereinbefore. In this case, both the ultrasonic transmitter and the ultrasonic receiver are positioned behind a protective plate. The emitted ultrasonic beam and the reflected ultrasonic beam are reflected by the mirror at 45°. Thus, the examining machine is preferably used in the case of irradiated assemblies.

BRIEF DESCRIPTION OF THE DRAWINGS

Various other objects, features and attendant advantages of the present invention will be more fully appreciated as the same becomes better understood from the following detailed description when considered in connection with the accompanying drawings in which like reference characters designate like or corresponding parts throughout the several views and wherein.

DETAILED DESCRIPTION OF THE PREFERRED EMBODIMENTS

Figure 1:
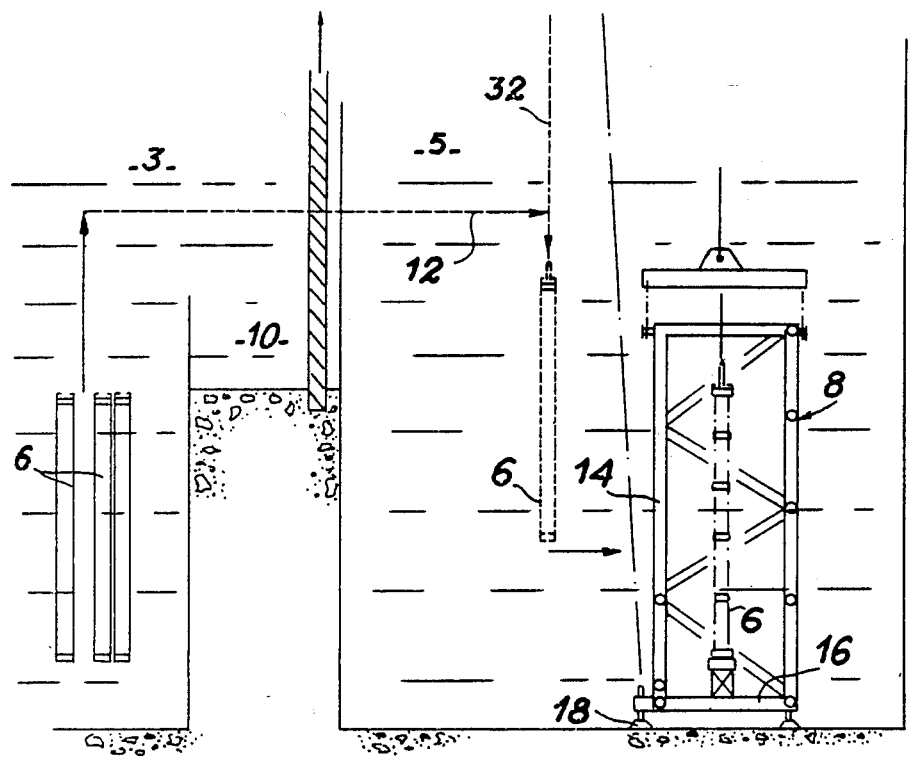
FIG. 1 is a general view of an examining machine for a fuel assembly diagrammatically showing the pool for the storage and transfer of fuel assemblies to the examining machine.

FIG. 1 shows diagrammatically and in section a fuel building. A large number of juxtaposed fuel assemblies 6 are located in a storage pool 3.

Every so often it is necessary to check certain assemblies during the use of the reactor. This checking operation is carried out by means of a fuel assembly examining machine 8 shown diagrammatically in FIG. 1. Machine 8 is located in a loading pit 5 for the transporting flasks. It comprises a tubular metal structure 14, which is made from stainless steel and fixed to a base plate 16, provided with three remotely regulatable jacks 18 making it possible to regulate its seating.

The transfer of each irradiated fuel assembly 6 takes place in boric acid solution 10, which makes it possible to follow the handling operations, whilst ensuring adequate protection against radiation and also effective cooling for the removal of residual heat.

Each fuel assembly 6 to be unloaded is raised by means of a handling machine (not shown), which moves above the level of the water. The fuel assembly is transferred underwater up to the examining machine 8. To avoid any unnecessary raising of assembly 6, the latter is introduced into the examining machine by a lateral groove and is then vertically introduced. Arrows 12 diagrammatically illustrate the path followed by a fuel assembly during a transfer from the storage pool 3 to machine 8.

The assembly is lowered into machine 8, which has guidance means for its base. These means are in the form of a hopper, with a square base, like the section of the assembly and which guide it on the support block.

Although FIG. 1 shows the case of using an examining machine for a fuel assembly according to the invention for checking irradiated fuel assemblies, it is obvious that it can also be used for checking new assemblies.

Figure 2:
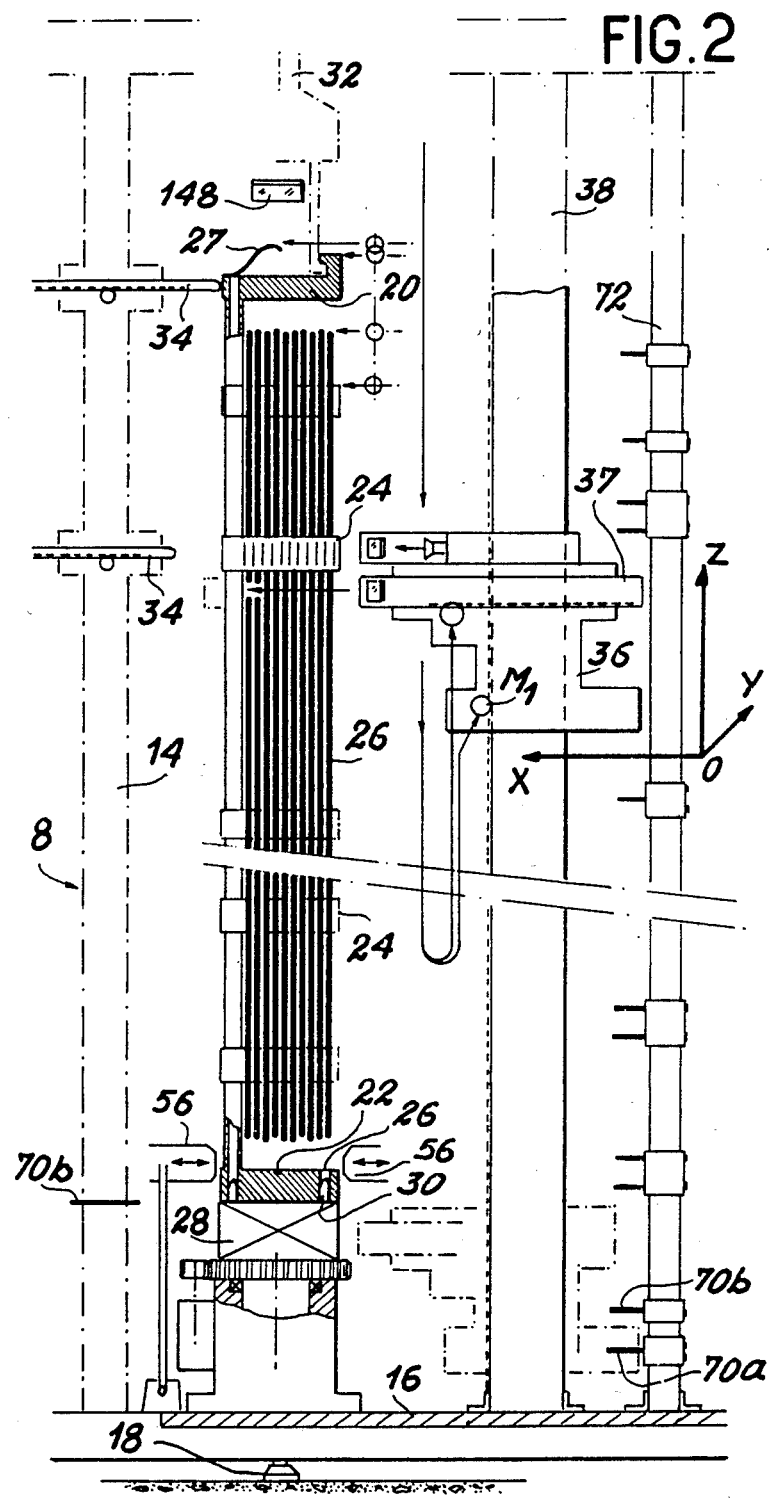
FIG. 2 is a side view of a fuel assembly examining machine according to the invention.

FIG. 2 is a larger scale side view in elevation of the examining machine according to the invention shown in FIG. 1. The tubular metal structure 14, which does not form part of the actual invention, has been diagrammatically shown in mixed line form. However, a fuel assembly 6 is shown in greater detail and machine 8 ensures its visual examination and metrology.

Assembly 6 comprises two rigid end members, an upper end member 20 and a lower end member 22. End members 20 and 22 are connected by a certain number of rigid guide tubes which form, with the end members, the assembly frame. A certain number of spacing grids 24 are mounted on the guide tubes and hold a group of fuel rods 26.

When placed in the core, assembly 6 is positioned between an upper plate and a lower plate forming part of internal structures within the reactor vessel. Each assembly is guided in translation by centering pins with respect to the core plates. For this purpose, the upper and lower end members 20, 22 respectively have two diagonally opposite holes 26 provided for the centering pins of the core plate.

Four springs 27 are provided on the upper end member 20 and serve to force assembly 6 against the lower plate of the core counter to the resulting hydraulic thrust which results, during the operation of the reactor, from the rising circulation of the cooling water between the fuel rods 26.

A rod of the handling machine 32 is fitted to the upper end member 20, so as to permit the handling of the assembly.

In conventional manner, machine 8 has examining means which are displaced relative to the assembly to be examined. These examining means, which will be described hereinafter, are carried by a moving carriage 36, which can be vertically displaced along axis OZ of a trirectangular trihedron OX, OY, OZ. An electric motor $M_1$ serves to vertically displace carriage 36 relative to a beam 38. Carriage 36 in turn supports a second carriage 37, which can be moved transversely with respect to carriage 36 along axis OX. An electric motor $M_2$ displaces carriage 37 relative to carriage 36.

The assembly 6 to be examined is positioned with respect to the reference system OXYZ. It is placed on support block 28, which constitutes a reference block for the measurements.

The positioning holes 26 for member 22 are used for positioning the assembly relative to support block 28. The latter has two centering pins 38, identical to the centering pins provided on the lower plate of the internal structures of the core and which are consequently fitted to the positioning holes 26 of the lower end member 22.

Two safety means are positioned at different levels and each of them is constituted by a pair of forks, located in each case on either side of the assembly.

According to the process for examining fuel assemblies of nuclear reactors according to the present invention, the assembly to be checked is vertically placed on support 28, assembly 6 being in equilibrium on the lower end member 22. Two safety forks 34, located at a given level are moved up, said forks being displaceable in translation. They surround assembly 6 without contact and form a ring around it, which can be continuous or broken, but which in all cases will prevent it from falling if it should move out of its position of equilibrium. The forks 34, diagrammatically indicated in FIG. 2, are shown in plan view in FIG. 4. The visual examining means are carried by a carriage 36, which moves on a vertical beam 38 having a rectangular cross-section. An electric motor is responsible for the displacement of carriage 36 relative to beam 38 via a winch and a chain (not shown). Forks 34 move back in an alternating manner to permit the passage of carriage 36, as well as the metrology and visual examination of the entire height of assembly 6.

The examination process according to the invention consequently provides an advantage compared with the presently known examining processes and machines. It makes it possible to examine the entire height of the assembly. However, the support members generally used for holding it at its two ends prevent the checking and inspection of the end members of the assembly 20, as well as that of springs 27.

Figure 4:
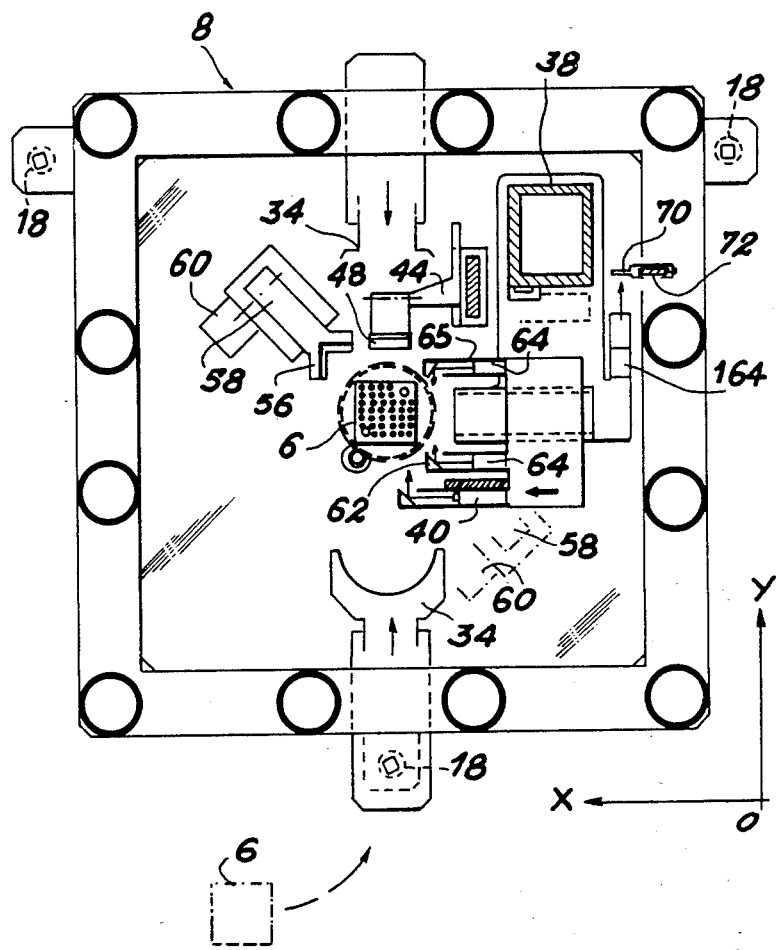
FIG. 4 is a plan view of the examining machine of FIGS. 2 and 3, which more particularly shows the safety forks and retractable centering device of the assembly base.

Machine 8 has visual observation means. These comprise a television camera 40, which can be moved transversely with respect to carriage 36, as can be seen in FIG. 4, which is a plan view of the examining machine 8 and make it possible to carry out a scan along axis OX.

Figure 3:
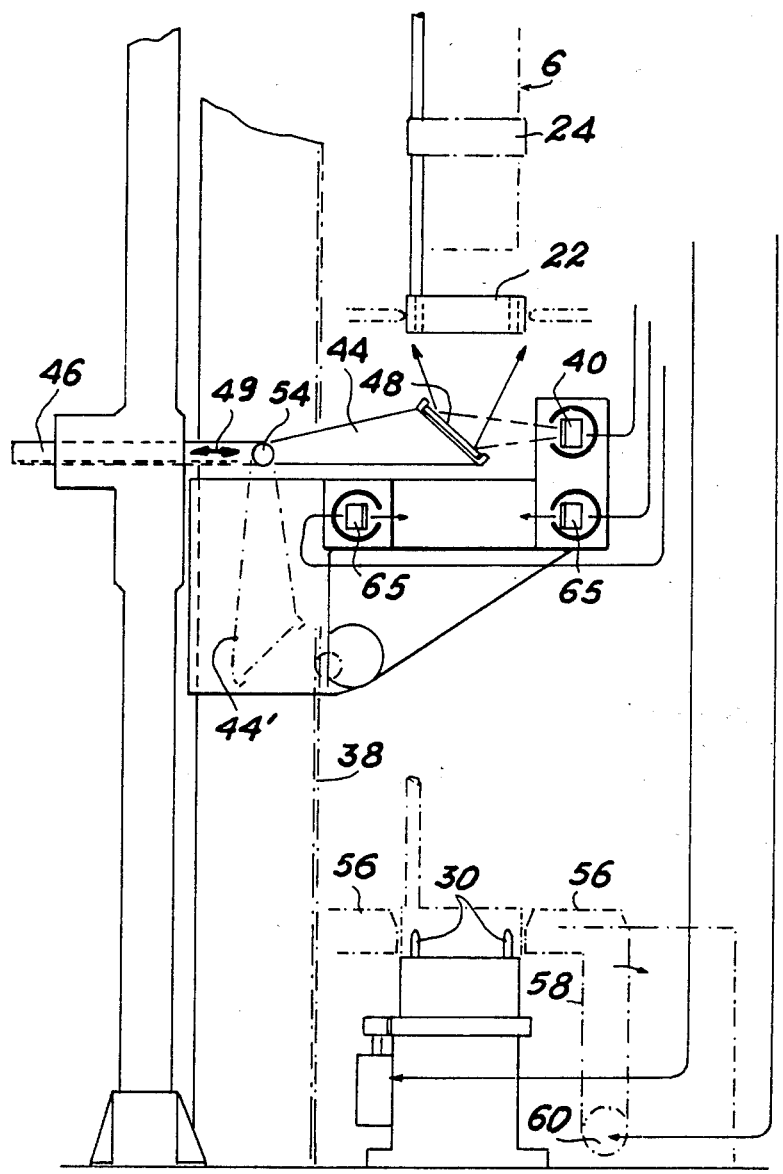
FIG. 3 is a simplified view of the machine of FIG. 2, more particularly showing the mirror permitting the examination of the base of the assembly and the device for centering the latter.

Mirror 48 carried by an arm 44 is located on the other side of the assembly with respect to camera 40. Arm 44 is integral with a carriage 46 displaceable along axis OX in order to retract mirror 48. In FIG. 3, this mirror is shown in the extended position. Mirror 48 makes it possible to visually observe the end of the lower end member 42 of the assembly.

There is also a retractable mirror 148 (diagrammatically shown in FIG. 2) placed in the upper part of machine 8 for examining the head of assembly 6 and springs 27. Mirror 148 can be manually raised by a rope connected to an arm (not shown), to which it is fixed.

FIG. 3 diagrammatically shows the end of assembly 6, with a lower spacing grid 24 for the fuel elements shown in mixed lines. Assembly 6 is suspended on rod 32 (cf. FIG. 2) of the handling machine and is kept at a suitable distance from mirror 38. Television camera 40, carried by examining carriage 36, is brought level with mirror 38, which makes it possible to examine the bottom of the assembly, as is diagrammatically indicated by arrow 42.

Mirror 48 is displaceable in translation, as is diagrammatically indicated by arrow 49. A motor 50 ensures the displacement in translation of carriage 46.

Preferably, the visual examination of the base of assembly 6 takes place at the time of raising it, i.e. at the end of the examination. Thus, the examination of the base must take place when the assembly is approximately at mid-height of machine 8. If carriage 46 is locked when the assembly was in this position, it would not be possible to carry out the remaining measurements. However, it is less prejudicial if carriage 46 locks at the time of raising assembly 6, because then all the other measurements have been carried out.

Moreover, a shearing pin is provided on spindle 54 of arm 44. If, as a result of an unsatisfactory operation, e.g. of the end of travel contacts, the assembly struck mirror 48, the pin would shear and the arm would pass by gravity into position 44', indicated by the dotted lines.

Furthermore, in order to permit the examination of the four faces of the lower part of the assembly, guidance means 56 are provided and are in several parts, e.g. two parts. Conventionally, the base of the assembly to be examined and in particular the lower end member, is centered by a frustum, which makes it possible to guide it until the centering pins 30 engage in positioning holes 26. However, in the case of the known devices, these guidance means for the base are not detachable, so that they are prejudicial to the observation of the lower part of the assembly, when the latter is in place. According to the invention, these guidance means 56 are in two parts, as can be seen in particular in FIG. 4. They are located at the end of an articulated arm 58, an electric motor 60 being responsible for the opening and closing of the two arms 58. FIG. 4 only shows one of these two arms, in order not to make the drawing too complicated. When they are moved together, they form a conical frustum with a square base, which ensures the guidance of the assembly during its presentation. Thus, as a result of this device, it is possible to examine the assembly when it rests freely on its base, which is the reference position used in metrology and without being disturbed by the guidance means.

The examining machine 8 also has further examining means. They are constituted by ultrasonic transmitter-receiver pairs. An ultrasonic transmitter-receiver pair makes it possible to determine in a single measurement, the position of a rod 26 or some other part of the assembly along axes OX and OY. It is displaced along axis OX (cf. FIG. 5). When it passes in front of part of the assembly, the echo is received by the receiver and is then associated with the coordinates of the machine, supplied by various coders (angular position of the support block 28, position at Z of carriage 36 and position at X of carriage 37) of the machine, it then being recorded on a magnetic support and displayed. In the case of an examination of fuel rods, the echo received is at a maximum when the transmitter-receiver pair is level with the geometrical axis. The determination of this maximum consequently makes it possible to deduce the true position of rod 26 along axis OX.

Moreover, the duration of the outward and return path of the ultrasonic beam makes it possible to deduce the position along axis OY of a rod or a random part, e.g. the position 68 of rod 26'.

Thus, it is possible to deduce in a single passage along axis OX, the absolute position at X and Y of each rod of a peripheral row.

There are two focused transducers (transmitter-receiver pair) arranged in facing manner on either side of assembly 6, which make it possible to simultaneously inspect two faces. In normal time, each transducer operates in transmission-reception. However, during part of the measuring cycle, the opposite transducers are made to operate, one as a transmitter and the other as a receiver, in order to calculate the corrections to be made in the case of a variation of the ultrasonic velocity in the medium under various influences, such as for example the temperature and the boron concentration.

A third focused ultrasonic transducer 164, called the standard pair or reference transducer, moves vertically and integrally of carriage 36 in front of a fixed rule 72 carrying horizontal marks 70. This transducer makes it possible to have an absolute definition in Z of the start and finish of the areas to be examined (e.g. grids) whilst also ensuring the synchronization of the electronics for measuring the transit times in water of the ultrasonics (synchronization of the validation signals of the echoes).

Another problem encountered in the visual examination and metrology of irradiated assemblies results from the radiation emitted by them. The intensity of this radiation is such that the observation or metrology means used have a reduced service life under the special operating conditions of the machine (close-up examination of irradiated and only very slightly cooled assemblies, i.e. after only a short decay time).

Thus, the invention also relates to a device for protecting the examining means, obviating the aforementioned disadvantage.

Figure 5:
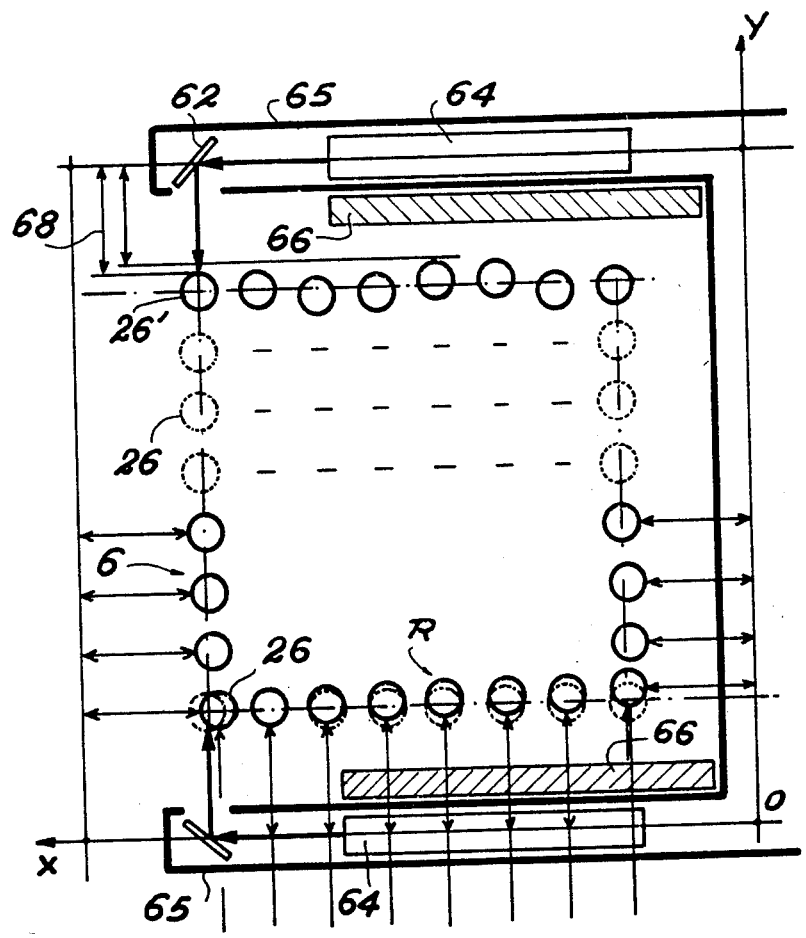
FIG. 5 is a plan view of part of the examining machine according to the invention illustrating the ultrasonic measuring process of the invention.

FIG. 5 shows the construction of this protective device applied to ultrasonic transmitter-receiver pairs 64. Assembly 6 is shown in cross-sectional form and only the outer rods 26 appear.

The two arms 65 are displaceable on either side of the assembly 6, in the direction of axis OX. At the end of each arm 65, there is a mirror 62, oriented at 45° relative to the axis OX. Each mirror 62 limits the importance of the radiation received by the transducer, but reflects the ultrasonics. Thus, the ultrasonic beam is reflected by 90° on the outward path, reflected by rods 26 or some other member and then reflected by 90° in the reverse direction after being received. Mirror 62 is, for example, a titanium mirror.

A protective device 66 is inserted between the examining means 64 and the irradiated assembly 6. This protection device 66 is, for example, constituted by a shell made from Denal, which is a fritted tungsten alloy.

As there are two measuring arms 65, it is possible to deduce in a single passage the measurements on the two opposite faces. By pivoting the assembly by 90° by rotating support block 28, the measurements are obtained on the two other faces.

The advantages of the ultrasonic measuring process according to the invention are as follows. It firstly makes it possible to perform a measurement without contact, particularly with fuel rods 26. This represents an advantage compared with mechanical sensors, which can cause faults to start on the fuel rod sheaths. Thus, they cannot be used on an irradiated assembly, which has been embrittled by said irradiation. Moreover, the image supplied by a television camera is highly dependent on the illumination and an particular does not make it possible to accurately determine the axis of a rod. However, the ultrasonic measuring device does not suffer from this disadvantage and ensures greater accuracy than that obtained with a television camera. Finally, with a television camera, it is only possible to examine one face at once, because the simultaneous illumination of two opposite faces would be prejudicial to observation.

All the information received by the ultrasonic sensors and the running coordinates are recorded for their subsequent processing. This is carried out by an informatics system, which passes outside the scope of the invention and will not be described. However, it is pointed out that the informatics system can supply an instantaneous representation of the areas to be examined during the development of the examination and that the processing of data received makes it possible to deduce all the information which is required in connection with the assembly, e.g. the spacing between two rods, the distance between the top of a rod and an end plate, the bending of a rod or the kinking of the assembly. For example, in the case of a row R shown in FIG. 5, the measurement of the position of the rods makes it possible to establish an increasing displacement of the true position of the fuel rods relative to their theoretical position, the true position being shown in thick lines, whereas the theoretical position is shown in thin lines. It can be deduced therefrom that there has been a kinking of the fuel assembly during its use.

The measurement described hereinbefore for a given level can obviously be repeated at different levels. The displacement of the carriage on the vertical beam 36 is controlled by marks on a vertical graduated rule, which serves as a reference. The standard transducer, integral with the carriage 36 supplies a signal when it passes in front of a mark 70. The detection system of the marks 70 operates on the basis of a principle identical to that of a system for detecting the position of the axes of rods 26 described hereinbefore. Thus, it is possible to accurately know the corresponding position of the two transmitter-receiver transducers 64 performing the measurements on the fuel assembly. For example, a row of marks 70 is shown. The lower mark 70a corresponds to a position of probe 64a facing the reference block 28. Mark 70b corresponds to reference O, i.e. to the upper face of reference block 28. The four marks 70A, B, C, D define two inspection areas, namely areas AB and CD of the sound detector.

It is known that the propagation rate of the ultrasonic waves in a coupling medium, water in the case of the examining machine 8 according to the invention, is dependent on a certain number of parameters, such as e.g. the temperature of the water or its boron concentration. Remembering that the accuracy of the measuring process according to the invention is dependent on the accuracy with which the ultrasonic propagation rate in water is known, it is necessary to correct this value as a function of the various parameters on which it depends. For example, the irradiated assembly 6 gives off a large amount of heat, which reheats the water in which it is immersed. Thus, there is a high temperature gradient about the assembly to be examined.

Thus, the invention relates to a process for using an examining machine, which takes account of the true propagation rate of the ultrasonic waves in the liquid coupling medium located between the transmitter and the receiver. In order to accurately determine this propagation rate, one of the ultrasonic transmitters-receivers (transducers) 64 located in one of the arms 65 is made to operate as a transmitter and the other transmitter-receiver pair (transducer) 64 located in arm 65 on the other side of the assembly to be examined is made to operate as a receiver. The first ultrasonic transducer 64 transmits an ultrasonic wave, e.g. a pulse, which is received by the second transducer 64. The distance between the transmitter and the receiver is a characteristic of the machine and is very accurately known. In the case of the embodiment of FIG. 5, this distance takes account of the complete passage of the wave before and after reflection on the two mirrors 62. As the distance covered by the ultrasonic wave is known, it is possible to deduce therefrom its propagation rate in water. Consequently it is possible to correct the distance measurements in X and Y of a constituent part of the assembly, such as a rod or grating, in accordance with the process described hereinbefore.

This correction of variations in the propagation rate of ultrasonic waves in the liquid coupling medium can be carried out between each measurement, e.g. on scanning two lateral faces of assembly 6 for measuring the positions in X and Y of fuel rods 26. Thus, when carriage 37 moves in accordance with axis OX, the ultrasonic beam passes in front of a row of fuel rods 26, then in front of the gap separating two rows of rods. At this time, there is no obstacle (unless the assembly is highly kinked) between the two mirrors 62. Thus, it is possible to operate the examining machine in the manner described hereinbefore, in which one of the pairs acts as a transmitter and the other as a receiver, which makes it possible to perform the correction of the propagation rate of the ultrasonic waves in the liquid medium. In the case of excessive kinking of the assembly, it is possible to carry out this correction at the start and finish of the scan of carriage 37, because its travel passes beyond the size of the assembly.

The examining machine according to the invention also has a third ultrasonic transducer 164 (transmitter-receiver pair), called the reference pair in the remainder of the text, and a vertical standard rule 72 on which are placed reference marks 70. As can be seen in FIG. 5, these marks define inspection areas. Thus, marks 70a and 70b define an inspection area, whilst marks 70c and 70d define a second inspection area of a grid.

The reference transmitter-receiver pair 164 is directed towards marks 70. The ultrasonic waves which it transmits are reflected by these marks, when the vertically moving carriage 36 passes in front of one of them. In view of the fact that the position of these marks 70 is very accurately known, the reception of the ultrasonic echo makes it possible to accurately determine the position of carriage 36 relative to the marks of the standard rule and consequently supplies absolute reference dimensions in Z of the areas to be examined.

These absolute reference dimensions can be used for periodically readjusting or recalibrating coder Z. Thus, it is known that the examining machine comprises three coders, a coder in X, a coder in Z and an angular coder of the position of support block 28. At all times, each coder gives the coordinates of the machine, i.e. the coordinates in X and Z of carriages 37 and 36 respectively, and the angular position of support block 28. However, a certain error or drift may be introduced into the information supplied by the coders. In particular, carriage 36 has a long travel and there can be a variation or error of the coder between the ends of said travel. The reference transmitter-receiver pair 164 makes it advantageously possible to readjust the information supplied by coder Z on the absolute position along axis OZ of the carriage 36, which it regularly supplies, particularly at the start and finish of each area to be examined.

Moreover, the distance between the transmitter-receiver pair 164 and the marks 70 of rule 72 is very accurately known, because it is a characteristic of the machine. The duration of the outward and return path of the echo of the reference pair 164 makes it possible to deduce the propagation rate of the ultrasonic waves in the coupling medium. The value of this propagation speed can also be used for carrying out corrections on the wave propagation rate. In this case, it will not be necessary to use the arrangement described hereinbefore in which one of the transmitter-receiver pairs 64 functions as a transmitter and the other as a receiver.

The duration of the outward and return path of the wave transmitted by the reference pair 164 can also be used for the validation of the echo received by each of the transmitter-receiver (transducer) pairs 64 performing the measurements at X and Y in accordance with the process of the invention. More specifically, this makes it possible to determine the position of the validation gate of the echo received by the pair 64. Thus, it is known that these measuring pairs 64 receive multiple echoes and not a single echo, because the ultrasonic signal is itself subject to multiple reflections. It is therefore necessary to validate the echo received by means of a validation gate in which is normally present the echo corresponding to a single outward and return path of the wave of pair 64 with respect to the object whose position is to be determined. Obviously the positioning of the validation gate takes account of the ultrasonic wave propagation speed in the liquid coupling medium. However, this speed can vary, as has been stated hereinbefore. It is therefore necessary to correct the position of the validation gate, as a function of the propagation speed. This is obtained on the basis of information from the reference pair 164, which makes it possible to correct the position of the gate, as a function of the wave propagation speed variations in the coupling medium.

Thus, the examining machine makes it possible to visually examine the six faces of the assembly by means of a television camera and its metrology. Two retractable mirrors, respectively a top mirror and a bottom mirror, make it possible to examine the top and bottom of the assembly. The examining machine in particular makes it possible to measure the height of the assembly, the spacing between the ends of the peripheral rods and the end members 20, 22, the position of grids 24, the position of the axis of outer rods 26, the height of springs such as spring 27, as well as the arching and kinking of the assembly.

Obviously, numerous modifications and variations of the present invention are possible in light of the above teachings. It is therefore to be understood that within the scope of the appended claims, the invention may be practiced otherwise than as specifically described herein.

What is claimed is:

1. A machine for examining a fuel assembly of a nuclear reactor, comprising:
   a plate;
   a structure mounted on said plate;
   a support block pivotably fitted on said plate and on which the fuel assembly is placed vertically;
   a carriage slidably fitted on said structure;
   means mounted on said carriage for examining the fuel assembly;
   guidance means for guiding the fuel assembly with respect to the support block; and
   a plurality of safety devices respectively located at a plurality of predetermined levels on said structure, each of said safety devices being positioned at a distance from the fuel assembly and including means for retaining said fuel assembly in an equilibrium position, said means for examining the fuel assembly being displaceable along the complete height of the fuel assembly.

2. A machine according to claim 1, wherein said plurality of safety devices further comprise at least one pair of forks, said pair of forks being displaceable with respect to said structure so as to be placed around the fuel assembly and to restrain the fuel assembly upon the fuel assembly moving out of said equilibrium position.

3. A machine according to claim 2, further comprising a second pair of forks for alternately being retracted to permit the passage of said carriage.

4. A machine according to claim 1, wherein said guidance means further comprises at least first and second guidance parts wherein said guidance parts are movable away from the base of the fuel assembly after the fuel assembly has been placed in said equilibrium position for examination of the complete height of the fuel assembly.

5. A machine according to claim 1, further comprising a wave transmitting source directed towards the assembly, a mirror inclined so as to reflect waves reflected by the fuel assembly towards the means for examining the fuel assembly and means positioned between the fuel assembly and the means for examining the fuel assembly for protecting the means for examining the fuel assembly against radiation emitted by the fuel assembly.

6. An examining machine according to claim 5, wherein the wave transmitting source further comprises a light source and wherein the means for examining the assembly comprises a television camera.

7. An examining machine according to claim 5, wherein the wave transmitting source further comprises an ultrasonic transmitter and the means for examining the fuel assembly further comprises an ultrasonic receiver.

8. A machine according to claim 5, wherein the wave transmitting source further comprises an ultrasonic transmitter having a vertically displaceable transmitter-receiver pair and wherein the means for examining the fuel assembly further comprises an ultrasonic receiver wherein the transmitter transmits an ultrasonic beam in the direction of the fuel assembly and variations of an echo received when the transmitter-receiver pair is displaced vertically relative to the assembly allows for a determination of the position of different constituent parts.

9. A machine according to claim 8, wherein a distance separating the transmitter-receiver pair from the part of the assembly which has reflected the ultrasonic beam is determined by measurement of the duration of an outward and return path of the ultrasonic beam of said ultrasonic transmitter.

10. An examining machine according to claim 5, wherein said means for protecting the means for examining the fuel assembly against radiation emitted by the assembly further comprises a tungsten alloy cell.

11. An examining machine according to claim 8, wherein said means for examining the fuel assembly further comprises a reference transmitter-receiver pair and a vertical standard rule having reference marks placed at the top of a start and finish of areas to be examined, the reference pair being directed towards the marks of the standard rule and supplying, by reflection of the ultrasonic echoes of said marks, absolute reference dimensions of the areas to be examined in the direction of a predetermined axis.

12. An examining machine according to claim 11, wherein a distance between the reference transmitter-receiver pair and said marks is predetermined and wherein an echoe received by the measurement transmitter-receiver pairs of the machine is validated by a validation gate within which said echo must be located in order to be retained, the position of said validation gate being determined as a function of the duration of an outward and return path of said echo from said reference pair to said marks of the standard rule.

13. A process for examining a fuel assembly, which comprises:
placing said fuel assembly on a support block so as to allow the fuel assembly to rest freely thereon in a vertical equilibrium position;
contacting said fuel assembly with a safety mechanism upon shifting of said fuel assembly from said equilibrium position, said safety mechanism comprising a plurality of safety devices respectively located at a plurality of predetermined levels, each of said safety devices being positioned at a distance from the fuel assembly and including the step of retaining the fuel assembly in an equilibrium position; and
examining said fuel assembly with an examination mechanism displaceable along the complete height when said fuel assembly is in said equilibrium position.

14. A process for examining a fuel assembly as set forth in claim 13, which further comprises moving the safety mechanism apart so as to allow for passage of said examination mechanism prior to examination of said fuel assembly.

15. A process for examining a fuel assembly according to claim 13, wherein the examination machine includes two ultrasonic transducer-receiver pairs located on either side of the fuel assembly to be examined, the distance between the two transmitter-receiver pairs being predetermined and wherein a first pair of the transmitter-receiver pairs functions as a transmitter while a second pair functions as a receiver, which further comprises:
measuring the propagation time of an ultrasonic wave in a coupling liquid medium from the first to the second transmitter-receiver pair;
determining the propagation speed of ultrasonic waves in said coupling liquid medium; and
correcting measurements of the examining machine as a function of said propagation speed.

16. A process according to claim 15, which further comprises determining the propagation rate of said ultrasonic waves in said liquid coupling medium on the basis of the duration of an outward and return path of an echo of said transmitter-receiver pairs with respect to marks on a standard rule; and
correcting the measurements of the transmitter-receiver pairs on the machine as a function of the propagation rate.

* * * * *